United States Patent
Columbo et al.

[11] Patent Number: 6,099,455
[45] Date of Patent: Aug. 8, 2000

[54] RADIOISOTOPE STENT WITH NON-RADIOACTIVE END SECTIONS

[75] Inventors: Antonio Columbo, Gallarate, Italy; Robert E. Fischell, Dayton, Md.

[73] Assignee: IsoStent, Inc., Belmont, Calif.

[21] Appl. No.: 09/198,966

[22] Filed: Nov. 25, 1998

[51] Int. Cl.[7] .................................................. A61N 5/00
[52] U.S. Cl. ................................................................ 600/3
[58] Field of Search ............................ 600/1–8; 606/78, 606/108, 191, 194, 195, 198

[56] References Cited

U.S. PATENT DOCUMENTS

| 5,059,166 | 10/1991 | Fischell et al. | 600/3 |
| 5,840,009 | 11/1998 | Fischell et al. | 600/3 |
| 5,882,291 | 3/1999 | Bradshaw et al. | 600/3 |

Primary Examiner—Cary O'Connor
Assistant Examiner—Catherine McPherson

[57] ABSTRACT

A radioisotope stent that is made radioactive for most of the stent's length at a center section of the stent, but is not radioactive for a limited length at each end section of the stent. Such a stent design would have a negligible radiation level at the extreme ends of the stent. Therefore, there will not be any portion of the dilated stenosis that has no mechanical support from the stent and is also exposed to a moderate level of radiation. Furthermore, all portions of the dilated stenosis that are exposed to a high or moderate level of radiation will be mechanically supported by the stent so as to preclude the phenomena of late vascular contraction. Thus it is an object of this invention to have a stent that is designed with a comparatively high level of radioactivity at a longitudinally central section of the stent and would be free of any radioactivity at each of the two end sections of the stent.

16 Claims, 1 Drawing Sheet

RADIOISOTOPE STENT WITH NON-RADIOACTIVE END SECTIONS

BACKGROUND OF THE INVENTION

Recent data obtained from animal and human trials that expose dilated stenoses in arteries to both dilatation and ionizing radiation have shown that, after an extended time period such as six months, the section of the artery exposed to both dilatation and radiation exhibits the phenomena of late vascular contraction. A well known method to essentially eliminate late vascular contraction is to insert a stent into the artery at the site of the dilated stenosis.

Prior art radioisotope stents such as those described in U.S. Pat. No. 5,059,166 by R. E. Fischell, et al have been placed in both animal and human arteries. Although the results obtained from these studies have often shown very little cellular proliferation within the stent itself, especially at comparatively high activities for the radioisotope stent, there has been considerable vascular narrowing observed just beyond the edges of the stent. Much of this vascular narrowing is due to late vascular contraction that is caused by a combination of vascular trauma and a moderate level of radiation.

SUMMARY OF THE INVENTION

The present invention is designed to overcome the shortcomings of the prior art radioisotope stents. Specifically, the present invention is a radioisotope stent that is made radioactive for most of the stent's length at a center section of the stent, but is not radioactive for a limited length at each end section of the stent. Such a stent design would have a negligible radiation level at the extreme ends of the stent. Therefore, there will not be any portion of the dilated stenosis that has no mechanical support from the stent and is also exposed to a moderate level of radiation. Furthermore, all portions of the dilated stenosis that are exposed to a high or moderate level of radiation will be mechanically supported by the stent so as to preclude the phenomena of late vascular contraction.

Thus it is an object of this invention to have a stent that is designed with a comparatively high level of radioactivity at a longitudinally central section of the stent and would be free of any radioactivity at each of the two end sections of the stent.

Another object of this invention is to have a radioisotope stent that does not cause late vascular contraction within an artery at sites just distal or just proximal to the implanted stent, i.e., just beyond the proximal and distal edges of the stent.

These and other objects and advantages of this invention will become obvious to a person of ordinary skill in this art upon reading of the detailed description of this invention including the associated drawings as presented herein.

DETAILED DESCRIPTION OF THE DRAWINGS

Figure 1:
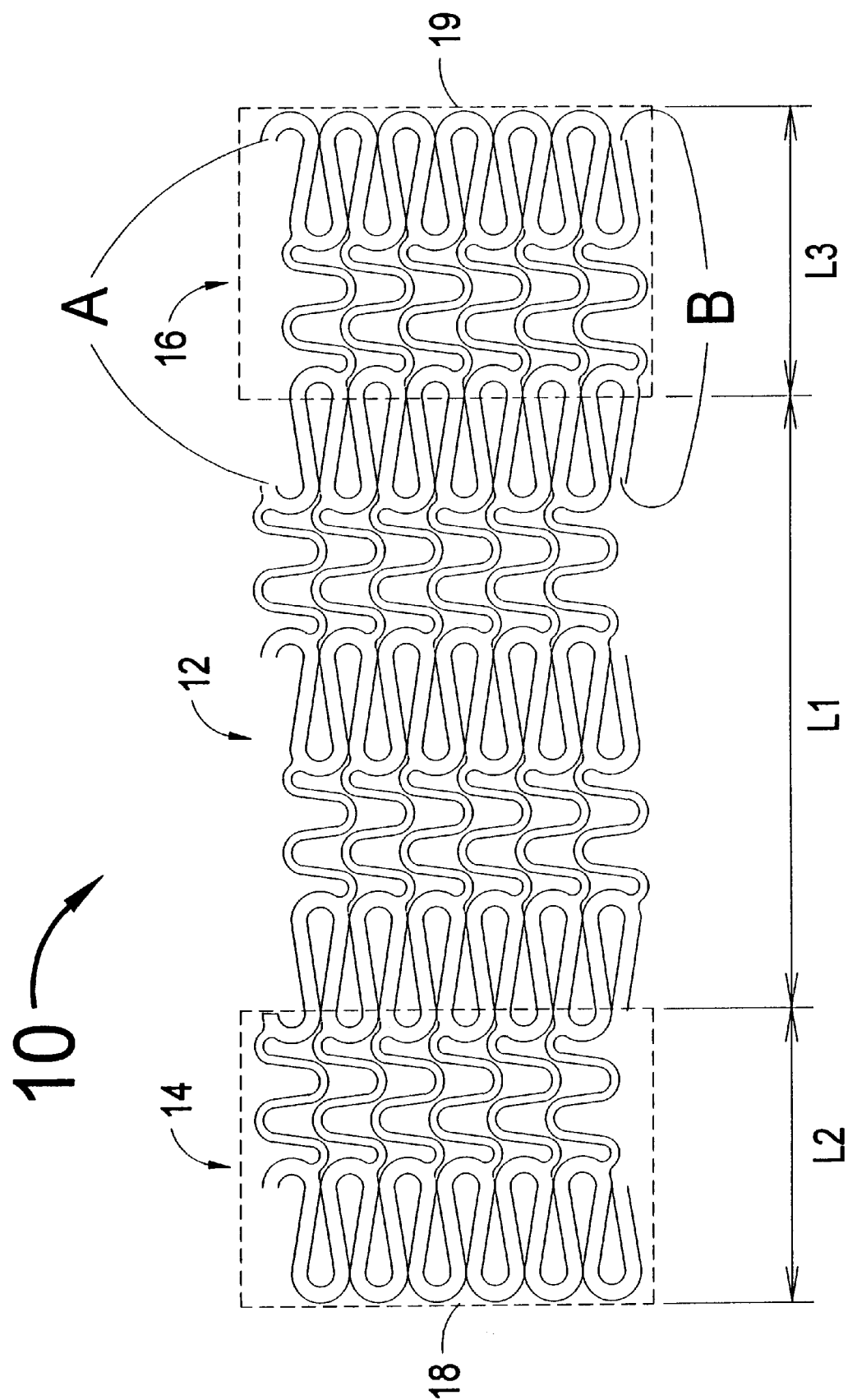
FIG. 1 is a flat, layout view of a cylindrical stent indicating a central section having a length L1 that is made radioactive and two end sections; a proximal end section of length L2, and a distal end section of length L3, with neither end section being made radioactive.

FIG. 1 is a flat, layout view of the stent 10 which has a radioactive central section 12 having a longitudinal length L1, a non-radioactive proximal end section 14 having a length L2 and a non-radioactive distal end section 16 having a length L3. The stent 10 is of conventional design which is a cylindrical, thin-walled, metal structure with the points "A" being connected to the points "B". A typical overall length for such a stent would be 20 mm. Such a stent would typically have a length L1 that was between 10 and 18 mm. Typically, the length L2 would be approximately equal to the length L3. If L2=L3, then for a 20 mm long stent, the length L2 (or L3) would be given by L2=1/2 (20- L1). For example, if L1=12 mm, then L2=L3=4 mm.

For this invention to function properly, the length of the central section 12 of the stent 10 should be between 20% to 90% of the total length of the stent 10, and the length of each section 14 and 16 should be between 5% and 40% of the total length of the stent 10.

Since the radioisotope phosphorous-32 has a range in human tissue of only about 3.5 mm for 90 percent of its beta particles, a stent 10 with an L2 or L3 value of approximately 4 mm would have very little radiation dosage beyond the ends 18 and 19 of such a stent 10. Therefore, the value of 2 to 5 mm for the length L2 or L3 would be quite reasonable for a phosphorous-32 radioisotope stent 10 with non-radioactive end sections 14 and 16. Furthermore, a stent activity of phosphorous-32 between 1 and 50 microCuries would be a suitable level of radioactivity for the central section of such a stent.

For an isotope such as yttrium-90 which has a somewhat greater energy level for its emitted beta particles, a length for L2 or L3 of 3 to 6 mm would be more appropriate. For yttrium-90, a level of radioactivity between 2 and 100 microCuries would be suitable.

It should be understood that the central section 12 could be made radioactive with either an x-ray or gamma ray emitting radioisotope. Whatever radioisotope is used, the general rule would apply that the level of radiation at the stent's outer surface at the proximal end 18 and the distal end 19 should be between 1 and 30 percent of the level of radiation provided at the stent's outer surface at the longitudinal center of the stent 10. It should also be understood that the stent described herein could be either of the balloon expandable type or the self-expandable type.

Various other modifications, adaptations, and alternative designs are of course possible in light of the above teachings. Therefore, it should be understood at this time that within the scope of the appended claims, the invention can be practiced otherwise than as specifically described herein.

What is claimed is:

1. A stent having a thin-walled, cylindrical structure for implantation at the site of a vascular stenosis, the stent having a proximal end section that extends longitudinally for a length L2, a distal end section that extends longitudinally for a length L3, and a central section extending longitudinally for a length L1, the central section being situated longitudinally between the proximal end section and the distal end section, the central section of the stent being radioactive and both the proximal end section and the distal end section being non-radioactive.

2. The stent of claim 1 wherein the length of the proximal end section is approximately equal to the length of the distal end section.

3. The stent of claim 1 wherein the central section is made radioactive by the inclusion of a beta particle emitting radioisotope.

4. The stent of claim 3 wherein the beta particle emitting radioisotope is phosphorous-32.

5. The stent of claim 4 wherein the length of either end section is between 2 and 5 mm.

6. The stent of claim 4 wherein the phosphorous-32 has a radioactivity level between 1.0 and 50 microCuries.

7. The stent of claim 3 wherein the beta particle emitting radioisotope is yttrium-90.

8. The stent of claim 7 wherein the length of either end section is between 3 and 6 mm.

9. The stent of claim 7 wherein the yttrium-90 has a radioactivity level between 2.0 and 100 microCuries.

10. The stent of claim 1 wherein the central section of the stent is made radioactive by the inclusion of a radioisotope that is predominately a gamma ray emitter.

11. The stent of claim 1 wherein the central section of the stent is made radioactive by the inclusion of a radioisotope that is predominantly an x-ray emitter.

12. The stent of claim 1 wherein the stent has a distal end and a proximal end and a longitudinal center that is situated centrally between the distal end and the proximal end, and at the stent's outer surface, the level of radioactivity at the distal and proximal ends of the stent is between 1% and 30% of the level of radioactivity at the longitudinal center of the stent.

13. The stent of claim 1 wherein the length of the central section is between 20 and 90 percent of the total length of the stent.

14. The stent of claim 1 wherein the length of either end section is between 5 and 40 percent of the total length of the stent.

15. The stent of claim 1 wherein the stent is a balloon expandable stent.

16. The stent of claim 1 wherein the stent is a self-expandable stent.

* * * * *